(12) United States Patent
Carson et al.

(10) Patent No.: US 8,268,249 B2
(45) Date of Patent: Sep. 18, 2012

(54) ANALYTICAL DEVICE WITH LIGHTGUIDE ILLUMINATION OF CAPILLARY AND MICROGROOVE ARRAYS

(75) Inventors: Larry J. Carson, Maplewood, MN (US); Joel R. Dufresne, St. Paul, MN (US); Patrick R. Fleming, Lake Elmo, MN (US); Michael C. Lea, Bracknell (GB); Nicholas A. Lee, Woodbury, MN (US); John Shigeura, Portola Valley, CA (US)

(73) Assignees: 3M Innovative Properties Company, St. Paul, MN (US); Life Technologies Corporation, Carlsbad, CA (US)

( * ) Notice: Subject to any disclaimer, the term of this patent is extended or adjusted under 35 U.S.C. 154(b) by 1053 days.

(21) Appl. No.: 11/601,326

(22) Filed: Nov. 16, 2006

(65) Prior Publication Data
US 2007/0065344 A1   Mar. 22, 2007

Related U.S. Application Data

(63) Continuation of application No. 10/028,257, filed on Dec. 19, 2001, now Pat. No. 7,189,361.

(51) Int. Cl.
*G01N 21/03* (2006.01)
*G01N 21/76* (2006.01)
*G01N 21/00* (2006.01)
*G01N 27/00* (2006.01)
*G01J 3/00* (2006.01)

(52) U.S. Cl. ........ 422/82.05; 422/52; 422/68.1; 422/81; 422/82.06; 422/82.07; 422/82.08; 422/82.09; 422/82.11; 436/164; 436/171; 436/172; 204/452; 204/603; 385/38; 385/44; 385/83; 385/115; 356/300; 356/344; 73/1.01; 73/1.02; 73/1.56

(58) Field of Classification Search ................... None
See application file for complete search history.

(56) References Cited

U.S. PATENT DOCUMENTS

| | | | |
|---|---|---|---|
| 2,467,748 A | 4/1949 | Hittson | |
| 3,963,310 A | 6/1976 | Giallorenzi et al. | |
| 4,310,762 A | 1/1982 | Harris et al. | |
| 4,818,710 A * | 4/1989 | Sutherland et al. | 436/527 |
| 5,061,029 A | 10/1991 | Ishikawa | |
| 5,156,972 A * | 10/1992 | Issachar | 422/68.1 |
| 5,252,294 A | 10/1993 | Kroy et al. | |
| 5,268,080 A | 12/1993 | Kambara et al. | |

(Continued)

FOREIGN PATENT DOCUMENTS

JP      05-079469      3/1992

(Continued)

OTHER PUBLICATIONS

Anazawa et al., "A Capillary Array Gel Electrophoresis System Using Multiple Laser Focusing for DNA Sequencing," *Anal. Chem.*, 1996, 68:2699-2704.

(Continued)

*Primary Examiner* — Neil N Turk
(74) *Attorney, Agent, or Firm* — Shumaker & Sieffert, P.A.

(57) ABSTRACT

An analytical cell including a lightguide with a plurality of conduits filled with a migration medium. The medium, the lightguide and a surrounding medium have refractive indices selected such that light entering the lightguide is internally reflected within the lightguide to provide substantially uniform illumination of the conduits.

13 Claims, 14 Drawing Sheets

U.S. PATENT DOCUMENTS

| | | | |
|---|---|---|---|
| 5,274,240 | A | 12/1993 | Mathies et al. |
| 5,277,780 | A | 1/1994 | Kambara |
| 5,314,602 | A | 5/1994 | Kambara et al. |
| 5,324,401 | A | 6/1994 | Yeung et al. |
| 5,340,715 | A * | 8/1994 | Slovacek et al. ............. 435/6.11 |
| 5,413,686 | A | 5/1995 | Klein et al. |
| 5,414,508 | A | 5/1995 | Takahashi et al. |
| 5,439,578 | A | 8/1995 | Dovichi et al. |
| 5,498,324 | A | 3/1996 | Yeung et al. |
| 5,516,409 | A | 5/1996 | Kambara et al. |
| 5,529,679 | A | 6/1996 | Takahashi et al. |
| 5,582,705 | A | 12/1996 | Yeung et al. |
| 5,667,656 | A | 9/1997 | Kambara |
| 5,677,196 | A | 10/1997 | Herron et al. |
| 5,695,626 | A | 12/1997 | Yeung et al. |
| 5,741,411 | A | 4/1998 | Yeung et al. |
| 5,741,412 | A | 4/1998 | Dovichi et al. |
| 5,759,374 | A | 6/1998 | Takahashi et al. |
| 5,790,727 | A | 8/1998 | Dhadwal et al. |
| 5,833,827 | A | 11/1998 | Anazawa et al. |
| 5,938,908 | A | 8/1999 | Anazawa et al. |
| 5,954,932 | A | 9/1999 | Takahashi et al. |
| 5,964,998 | A | 10/1999 | Kambara |
| 6,064,784 | A | 5/2000 | Whitehead et al. |
| 6,464,852 | B1 | 10/2002 | Gorfinkel et al. |
| 6,542,691 | B2 | 4/2003 | Mizuno et al. |
| 6,611,634 | B2 | 8/2003 | Herron et al. |
| 6,613,212 | B1 | 9/2003 | Siebert et al. |
| 7,189,361 | B2 | 3/2007 | Carson et al. |

FOREIGN PATENT DOCUMENTS

| | | |
|---|---|---|
| JP | 09-096623 | 4/1997 |
| JP | 09-288088 | 11/1997 |
| JP | 10-170480 | 6/1998 |
| JP | 11-075812 | 3/1999 |
| WO | WO 98/10122 | 3/1998 |
| WO | 00/04371 | 1/2000 |

OTHER PUBLICATIONS

Anazawa et al., "A Capillary-Array Electrophoresis System Using Side-Entry On-Column Laser Irradiation Combined with Glass Rod Lenses," *Electrophoresis*, 1999, 20:539-546.

Huang et al., "Capillary Array Electrophoresis Using Laser-Excited Confocal Fluorescence Detection," *Anal. Chem.*, 1992, 64:967-972.

Huang et al, "DNA Sequencing Using Capillary Array Electrophoresis," *Anal. Chem.*, 19922, 64(18):2149-2154.

Kambara and Takahashi, "Multiple-Sheathflow Capillary Array DNS Analyser," *Nature*, 1993, 361:565-566.

Lu and Yeung, "Optimization of Excitation and Detection Geometry for Multiplexed Capillary Array Electrophoresis of DNA Fragments," *Applied Spectroscopy*, 1995, 49(5):605-609.

Lu and Yeung, "Side-Entry Excitation and Detection of Square Capillary Array Electrophoresis for DNA Sequencing," *J. Chromatography A*, 1999, 853:359-369.

Mathies and Huang, "Capillary Array Electrophoresis: An Approach to High-Speed, High-Throughput DNA Sequencing," *Nature*, 1992, 359:167-169.

Quesada et al., "Multi-Capillary Optical Waveguids for DNA Sequencing," *Electrophoresis*, 1998, 19:1415-1427.

Takahashi et al., "Multiple Sheath-Flow Gel Capillary-Array Electrophoresis for Multicolor Fluorescent DNA Detection," *Anal. Chem.*, 1994, 66:1021-1026.

Taylor and Yeung, "Multiplexed Fluorescence Detector for Capillary Electrophoresis Using Axial Optical Fiber Illumination," *Anal. Chem.*, 1993, 65:956-960.

Ueno and Yeung, "Simultaneous Monitoring of DNA Fragments Separated by Electrophoresis in a Multiplexed Array of 100 Capillaries," *Anal. Chem.*, 1994, 66:1424-1431.

* cited by examiner

ANALYTICAL DEVICE WITH LIGHTGUIDE ILLUMINATION OF CAPILLARY AND MICROGROOVE ARRAYS

This application is a continuation of and claims priority to Ser. No. 10/028,257, filed Dec. 19, 2001 now U.S. Pat. No. 7,189,361, the entire content of which is incorporated herein by reference.

TECHNICAL FIELD

This invention relates to methods and apparatus for detecting biological macromolecules.

BACKGROUND

Techniques for analyzing biological macromolecules, such as, for example, nucleic acids and proteins, have become increasingly important in the fields of medicine and genetics. One well accepted technique for analyzing biomolecules is gel electrophoresis. In gel electrophoresis a voltage is applied across at least one linear dimension of a medium, typically a liquid buffer or a polymer gel. A sample tagged with a fluorophore is introduced to the medium, and components of the sample separate under the influence of the applied electric field according to their respective electric mobilities. The fluorescently labeled components migrate down the linear dimension of the medium past a station where they are illuminated by a laser beam. Stimulated fluorescent emission from the illuminated components is captured by a detector as a function of time, producing an electropherogram that encodes the analytical information of interest.

Electrophoresis devices are available in a variety of formats. Traditionally, separations are performed in a medium made of cross-linked polymer matrix formed as a gel sheet, or slab gel, between two glass plates. To enable higher applied voltages, remove heat generated by electrophoretic currents, and provide higher throughput, the medium may be confined to narrow glass capillary tubes. Microgrooves fabricated into a planar, laminated substrate of glass or plastic have also been used as conduits for the medium.

In a high throughput analytical device, the capillaries or microgrooves, referred to herein as sample conduits, are arranged in substantially planar arrays so that many samples may be processed at the same time. The array format is most efficient when a single laser, or a small number of lasers, is used to illuminate the capillaries or microgrooves in the array. Since the medium in each conduit absorbs only a tiny fraction of the laser power, most devices utilize an arrangement in which the optical axis of the laser beam output is substantially coplanar with and normal to the longitudinal axes of the conduits. A single laser beam, or, in some cases opposed dual beams, impinge normal to the wall of the first conduit in a substantially planar array, illuminate the fluorescently labeled sample therein, exit the first conduit, propagate to the second conduit, and so forth. This technique has been generally successful for arrays with a small number of conduits, but becomes increasingly unworkable as the number of conduits in the array is increased. The variety of materials in the beam path (for example, glass, medium, air), each having its own index of refraction, as well as the multiplicity of surfaces, creates an extremely complex optical system. Reflection and refraction of the beam at the multiple surfaces diverts the beam from a direct passage though the conduits, which makes efficient and uniform delivery of the light to each conduit problematic.

The need for relative uniformity of illumination stems from the economical practice of using a single detector (or an array of identical detector elements) for measuring signal from each conduit of the planar array. As such, the signal from each conduit, proportional to the intensity of excitation, is detected with the same level of sensitivity and dynamic range. In this arrangement, nonuniform illumination would dictate undesirable trade-offs. For example, adjusting the intensity of the laser beam to achieve maximal sensitivity in a relatively poorly illuminated conduit could lead to detector saturation by signals of other, better illuminated conduits, thereby limiting the dynamic range of the better illuminated conduits. Therefore, array performance is optimized by ensuring that all conduits receive the same intensity of excitation light.

In each of these systems, the array of conduits is treated as a sequential optical system in which all or most of the light energy passing out of one conduit impinges on the next successive conduit in the array. These systems are extremely sensitive to optical misalignment and must be assembled to extremely high tolerances, so manufacturing yields would be expected to be quite low. In addition, this delicate optical system would be easily misaligned if repeatedly handled and installed in an analytical device.

The treatment of conduits as optical elements also places constraints in their geometry, depending on the optical properties of the materials used. For example, for capillaries in a close packed configuration, the ratio of the inner and outer diameters of the capillaries are restricted to a specific range, depending on the refractive indices of the capillary walls, the enclosed medium, and the surrounding medium. Capillaries with dimensions outside these ranges will fail to effectively transmit the beam from one capillary to the next. Optical alignment is not as significant a problem for microgrooves arrays, which may be precisely laid out equidistant from one another on a substrate. However, embossing and chemical etching procedures used to form the microgrooves in the substrate create beveled walls that are not perpendicular to the plane of the array or to the light source. When sealed with a coversheet and filled with a polymer medium, each microgrooves can form a prism-like optical structure that cumulatively causes the beam to deflect out of plane, leaving a majority of the microgrooves insufficiently illuminated.

Previous proposals for array illumination have made unacceptable compromises in illumination intensity or uniformity, or have demanded prohibitive requirements in optical alignment.

SUMMARY

In one embodiment, the invention is an analytical cell for detection of an analyte. The cell includes an elongate lightguide having an array of conduits extending therethough. The conduits are configured to support a migration medium. The lightguide and its surrounding medium have refractive indices selected such that light entering the lightguide is internally reflected within the lightguide to illuminate the conduits.

In a second embodiment, the invention is an analytical cell including a cover on a substrate. The substrate includes an array of substantially parallel grooves, wherein the grooves are substantially coplanar and are configured to support a migration medium. The migration medium, the substrate, the cover and the surrounding medium have refractive indices selected such that a lightguide is formed when the cover is placed on the substrate, and light entering the lightguide is totally internally reflected within the lightguide to illuminate the grooves.

In a third embodiment, the invention is an analytical device including an elongate lightguide. The lightguide includes a substrate with an array of substantially parallel grooves configured to support a migration medium, wherein the grooves are substantially coplanar and have a longitudinal axis in a first direction, and a cover on the substrate. A light source is placed outside the lightguide, wherein the source emits a light beam with an optical axis substantially coplanar with and normal to the longitudinal axes of the grooves. The migration medium, the substrate, the cover and a medium surrounding the substrate have refractive indices selected such that light emitted by the light source is totally internally reflected within the lightguide to illuminate the grooves.

In a fourth embodiment, the invention is an assay method including:

(a) providing an analytical cell including: (1) a substrate with a plurality of substantially parallel grooves, wherein the grooves are substantially coplanar, are configured to support a migration medium, and have longitudinal axes in a first direction, and (2) a cover on the substrate; wherein the migration medium, the substrate, the cover and a medium surrounding the substrate have refractive indices selected such that a lightguide is formed when the cover is placed on the substrate, and light entering the lightguide is internally reflected within the lightguide to illuminate the grooves;

(b) placing a sample on the migration medium in a groove, wherein the sample comprises a fluorescently labeled analyte;

(c) applying an electric field across the first direction to move the analyte in the groove;

(d) illuminating the lightguide with a light beam having an optical axis along a second direction substantially coplanar with the plane of the grooves and normal to the first direction, wherein the light entering the lightguide is totally internally reflected within the lightguide to illuminate at least a portion of each groove; and (e) detecting an emission from the analyte.

In a fifth embodiment, the invention is an analytical cell including a solid lightguide. The lightguide includes a first wall with a first interior surface, a second wall with a second interior surface, wherein the second wall is opposite the first wall, and the second interior surface faces the first interior surface, a third wall with a third interior surface, and a fourth wall opposite the third wall, and a surrounding medium adjacent at least one of the walls. The lightguide further includes a plurality of capillaries configured to support a migration medium, wherein the capillaries are fixed in an array at least partially enclosed within the lightguide, wherein the longitudinal axes of the capillaries are substantially parallel and coplanar. The migration medium, the capillaries, the lightguide and the surrounding medium have refractive indices selected such that light entering the lightguide is internally reflected within the lightguide at the interior surfaces to illuminate the capillaries.

In a sixth embodiment, the invention is an analytical cell including a lightguide. The lightguide includes a substrate with a plurality of substantially parallel grooves, wherein the grooves are substantially coplanar and have a substantially arcuate cross section, and a cover including an array of substantially parallel grooves corresponding to the grooves in the substrate, wherein the grooves in the cover are substantially coplanar and have a substantially arcuate cross section. A plurality of capillaries reside in the grooves between the substrate and the cover, wherein the capillaries have a substantially circular cross section, and the longitudinal axes of the capillaries extend in a first direction to form a substantially coplanar array, and wherein the capillaries are configured to support a migration medium. The migration medium, the capillaries, the substrate, the cover and a medium bordering the substrate have refractive indices selected light entering the lightguide from a second direction substantially coplanar with and normal to the first direction is totally internally reflected within the lightguide to illuminate the array.

In a seventh embodiment, the invention is an analytical device, including a lightguide. The lightguide includes a substrate with a plurality of substantially parallel grooves, wherein the grooves are substantially coplanar and have a substantially arcuate cross section, (2) a cover including a plurality of substantially parallel grooves corresponding to the grooves in the substrate, wherein the grooves in the cover are substantially coplanar and have a substantially arcuate cross section. A plurality of capillaries reside in the grooves between the substrate and the cover, wherein the capillaries have a substantially circular cross section, and the longitudinal axes of the capillaries extend in a first direction to form a substantially coplanar array, and wherein the capillaries are configured to support a migration medium. A light source is placed outside the lightguide, wherein the light source emits a beam having an optical axis substantially coplanar with and normal to the longitudinal axes of the capillaries in the array. The migration medium, the capillaries, the substrate, the cover and a medium bordering the substrate have refractive indices selected such that light emitted by the light source is totally internally reflected within the lightguide to illuminate the array.

In an eighth embodiment, the invention is an assay method including:

(1) providing an analytical cell including:

(a) a lightguide including (1) a substrate with a plurality of substantially parallel grooves, wherein the grooves are substantially coplanar and have a substantially arcuate cross section, and (2) a cover comprising a plurality of substantially parallel grooves corresponding to the grooves in the substrate, wherein the grooves in the cover are substantially coplanar and have a substantially arcuate cross section;

(b) a plurality of capillaries in the grooves between the substrate and the cover, wherein the capillaries have a substantially circular cross section, and the longitudinal axes of the capillaries extend in a first direction to form a substantially coplanar array, and wherein the capillaries are configured to support a migration medium;

(2) placing a sample on the migration medium in each capillary in the array, wherein the sample comprises a fluorescently labeled analyte;

(3) applying an electric field across the first direction to move the analyte in a capillary in the array;

(4) illuminating the lightguide with a light beam having an optical axis along a second direction substantially coplanar with the plane of the array and normal to the first direction, wherein the light entering the lightguide is totally internally reflected within the lightguide to illuminate at least a portion of the array; and (5) detecting with a detector an emission from the analyte.

In a ninth embodiment, the invention is an analyte separation device for the detection of one or more fluorescently labeled analytes, including (a) an elongate lightguide; (b) an array of conduits in the lightguide, wherein the conduits are configured to support a migration medium; (c) a light source optically coupled to the lightguide, wherein the lightguide has a refractive index greater than its surrounding medium such that light emitted by the source is totally internally reflected within the lightguide to illuminate the conduits; and (d) a detector optically coupled to the conduits.

With the invention, uniform illumination is achieved at a reasonable loss in intensity relative to direct illumination of a single capillary. In addition, the invention is very tolerant of errors in fabrication and operation, including, for example, misalignment of the light source, misalignment of the conduits in the array, and variations in channel bevel.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1A:
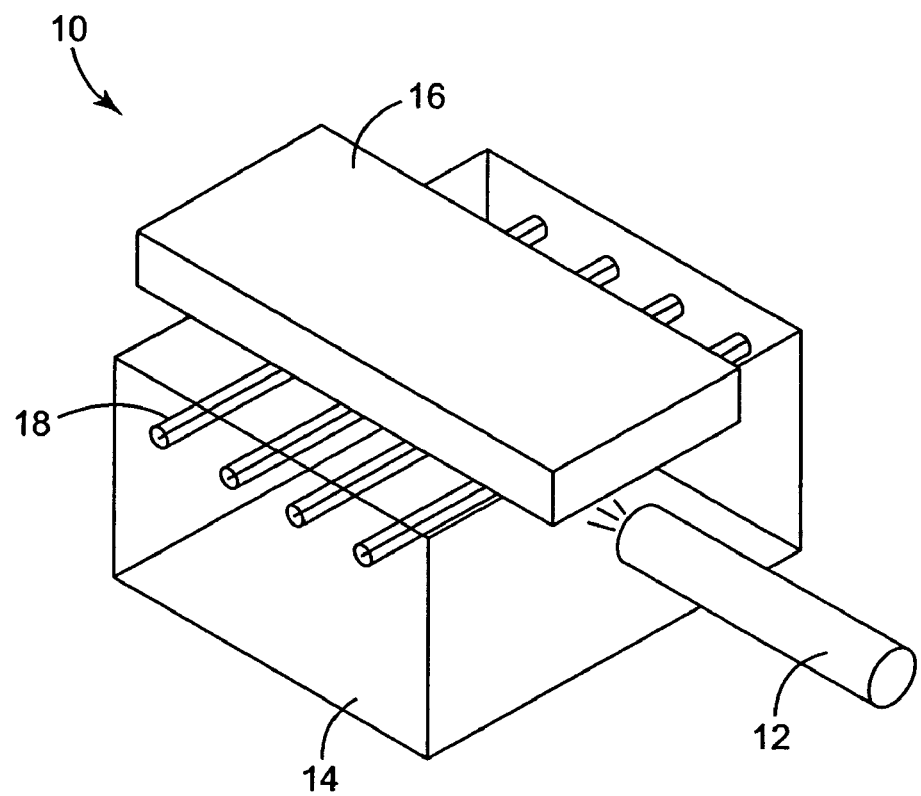
FIG. 1A is a schematic representation in perspective of an analytical device using the analytical cell of the invention.

FIG. 1A illustrates the major features of an embodiment of an analytical device of the invention. Generally, an analytical device 10 of the invention includes three principal components: a light source 12, an analytical cell 14 and a detector 16.

Referring to FIG. 1A, in one embodiment the cell 14 includes a plurality of conduits 18 with substantially parallel longitudinal axes. The conduits 18 are arranged in a substantially coplanar array, and are filled with a migration medium (not shown in FIG. 1A). When a fluorescently labeled sample is placed on the migration medium and an electric field is applied across a direction parallel to the longitudinal axes of the conduits, components of the sample migrate along the conduits and separate into a series of fluorescently labeled analytes. When a selected analyte enters the fluorescence detection cell 14, a light beam emitted from the light source 12 illuminates the cell 14. The beam from the light source 12 has an optical axis generally in the plane of the conduits 18 and normal to their longitudinal axes. When the light from the source 12 enters the cell 14, the light is totally internally reflected within the cell 14 to illuminate each of the conduits 18. The cell 14 acts as a lightguide that retains a substantial portion of the entering light and efficiently delivers it to each of the conduits in the array. Fluorescent emissions from the analyte are detected by the detector 16 to provide analytical information regarding the composition of the sample. The detector 16 may include one or more of the following elements: lenses and optical elements for collecting light from the cell 14, an aperture for exerting precise control over the spatial origin of light, diffraction gratings or prisms for spectral decomposition of the emitted light, and a two-dimensional photodetector such as a charge-coupled device (CCD) camera.

Figure 1B:
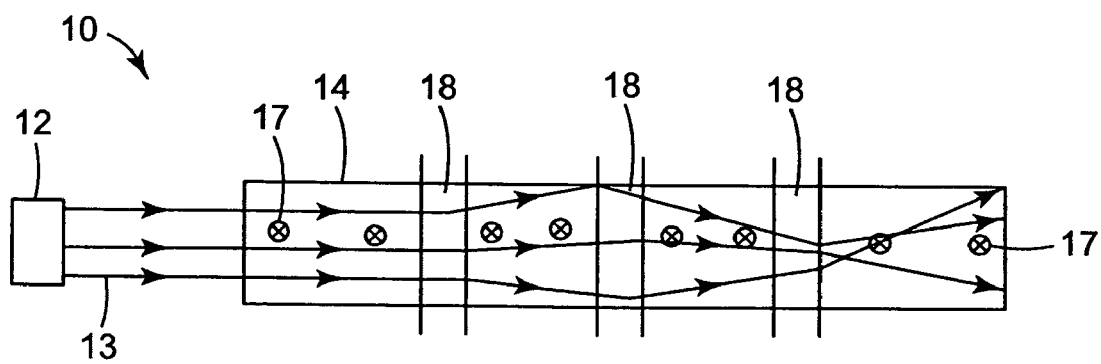
FIG. 1B is a schematic overhead view of an analytical device using the analytical cell of the invention.

As shown in FIG. 1B, the refractive index of the cell 14 may be selected with respect to the surrounding medium to confine the incoming light rays 13 from the source 12 to a specific volume. The optical intensity (power/unit volume) in this volume is sufficient to illuminate a selected portion of the each conduit 18 in the array and cause the analytes in that selected portion of each conduit to fluoresce. The fluorescent emissions 17 from the analytes then exit the illuminated volume and are detected by the detector 16 (not shown in FIG. 1B). The shape and dimensions of the illuminated volume may be controlled to contain the incoming light to provide an analytical device with a desired array size, throughput and resolution.

Figure 2A:
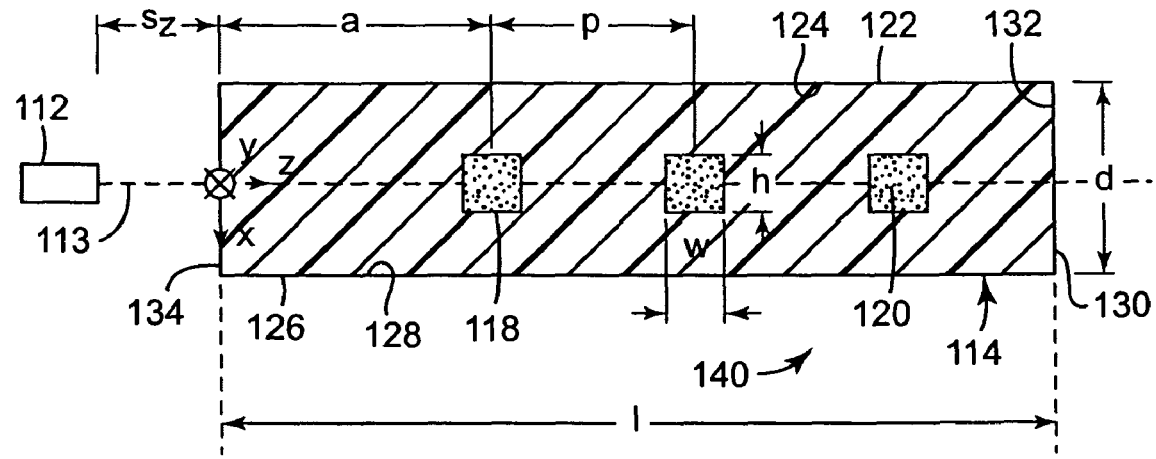
FIG. 2A is a cross sectional view of an analytical cell of the invention with microgrooves.

Referring to FIG. 2A, a cross-sectional view of an embodiment of an analytical cell 114 is shown. The cell 114 has a block-like shape with a substantially rectangular cross section having a length, l, measured in FIG. 2A along the z direction, which is substantially greater than its depth, d, measured along the x direction. The cell 114 includes three conduits 118 having a substantially square cross sectional shape with equal height h and width w. The longitudinal axes of the conduits 118 are substantially parallel to one another at a substantially equal pitch, p, and the conduits are arranged in a substantially coplanar array. Each conduit 118 is filled with a migration medium 120, which is typically a polymeric gel such as, for example, polyacrylamide.

In the embodiment shown in FIG. 2A the cell 114 includes a first wall 122 with a first internal surface 124, as well as a substantially parallel and opposed second wall 126 with a second internal surface 128 facing the first internal surface 124. The cell 114 further includes a third wall 130 that is generally normal to the planes of the first and second walls 122, 126. The third wall 130 has an internal surface 132. Any of the internal surfaces 124, 128 and 132 may be mirrored or at least partially reflective to reflect light back into the cell 114. Preferably, at least part of the surface 132 is a mirror.

A light source 112, typically a laser, emits a light beam 113 having an optical axis along the z direction and generally in the plane of the conduits 118. The light source 112 is a distance $s_z$ from the cell 114, and the light beam 113 enters the cell 114 at a fourth face 134 and travels along the z direction a defined distance, referred to herein as the atrium, a, until it reaches the first conduit in the array.

Light rays entering the cell 114 are internally reflected and remain confined to the cell 114 to allow substantially uniform illumination of all the conduits 118 in the array. Internal reflection in the cell 114 is achieved by, for example, selection of materials with appropriate refractive indices at the beam wavelength for the cell 114, the migration medium 120 and the surrounding medium 140 that is adjacent to at least one wall of the cell 114. Preferably, to achieve the most uniform illumination of all the conduits in the array, the refractive indices of the cell 114 and the migration medium 120 should match, or at least be as similar as possible. This reduces the diffusive effect of the surfaces encountered by the incoming light rays. The cell 114 is preferably made of a material that is transparent or translucent at the wavelength of the light emitted by the light source 112 and has low background fluorescence at the wavelength(s) of the sample fluorophor(s). The cell 114 is typically a block of glass or plastic, although one skilled in the art could select a wide variety of materials, depending on the wavelength emitted by the source 112, the refractive indices of the migration medium 120 and the surrounding medium 140, and the fluorescence properties of the material. Suitable materials for the cell 114 include, for example, fused silica glass, borosilicate glass, polycarbonate, polymethylmethacrylate, polymethylpentene, and cycloolefin copolymers.

The substantial internal reflection in the cell 114 is also achieved by selecting the shape and dimensions (length (l) and depth (d)) of the cell. The length and depth of the cell 114 illustrated in FIG. 2A are selected to provide a block-like shape, but many other shapes and length and/or depth variations may be used for the cell 114 depending on the intended application. For example, in a block like shape the overall level of illumination of the array typically decreases as the depth d of the cell increases. However, as the depth d decreases to approximately the dimension of the conduits, the illumination of the conduits nearest the light source will be significantly greater than the illumination of the conduits farthest from the light source, i.e. the illumination profile of the array will be more non-uniform. For example, for round cross section capillaries having an outside diameter of 120 µm spaced at a pitch of 240 µm in a cell of 200 µm depth, illumination varies about 25% across a 104 capillary array. If the thickness of the cell is increased to 300 µm, the variation in illumination is reduced to about 6%, but at a loss of intensity of about 25%. Therefore, in addition to the materials considerations discussed above, the overall dimensions of the cell may be selected to provide a predetermined illumination level and illumination profile required for a particular assay or a particular detector sensitivity level.

Figure 2B:
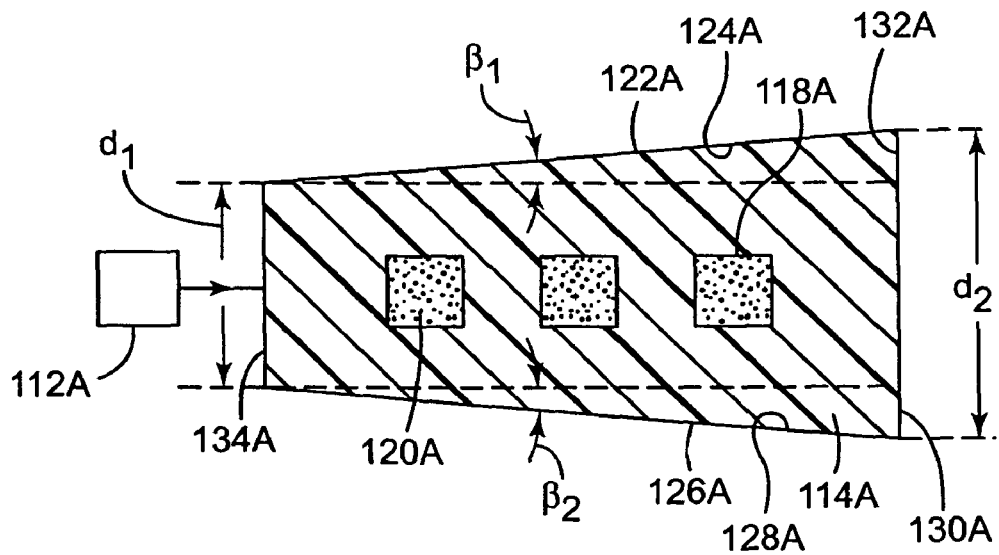
FIG. 2B is a cross sectional view of a trapezoidal analytical cell of the invention with microgrooves.

The overall shape of the cell 114 may also vary widely depending on the level of illumination and the illumination profile desired. For example, FIG. 2B shows a cell 114A with a generally trapezoidal cross sectional shape. The cell 114A includes three conduits 118A having a substantially square cross sectional shape with an equal height h and width w. The longitudinal axes of the conduits 118A are substantially parallel to one another at a substantially equal pitch, and the conduits are arranged in a substantially coplanar array. Each conduit 118A is filled with a migration medium 120A.

The cell 114A includes a first wall 122A with a first internal surface 124A, as well as an opposed second wall 126A with a second internal surface 128A facing the first internal surface 124A. The first wall 122A and the second wall 126A gradually diverge at angles $\theta 1$ and $\theta 2$, respectively. The cell 114A further includes a third wall 130A that preferably has a reflective internal surface 132A. A light source 112A emits a light beam 113A having an optical axis along the z direction and generally in the plane of the conduits 118A and substantially normal to the longitudinal axes thereof. The light beam 113A enters the cell 114A at a fourth face 134A. The face 134A has a depth $d_1$ that is less than the depth $d_2$ of the opposed face 130A. This trapezoidal cross-sectional shape tends to recapture light that normally would be refracted out of the cell 114A, which tends to provide more uniform illumination of the conduits farthest from the light source 112A. The trapezoidal shape provides more options when, for example, the refractive index of the cell 114A or the refractive index of the surrounding medium are limited to particular materials, or when there is a large refractive index mismatch between the cell 114A and the migration medium 118A.

The refractive index difference at the interface between the cell and the surrounding medium confines the light from the light source to the body of the cell. The surrounding medium is preferably air. However, the refractive index of the surrounding medium may also be selected to provide a particular level of illumination or illumination profile, and may have an impact on the materials selected for the cell, as well as its dimensions. For example, the cell 114 may be placed in a liquid or solid medium with a selected index of refraction, which may provide more flexibility in the selection of materials for the cell and the migration medium for a particular assay application or to adapt to a particular detector's dynamic range.

Figure 3:
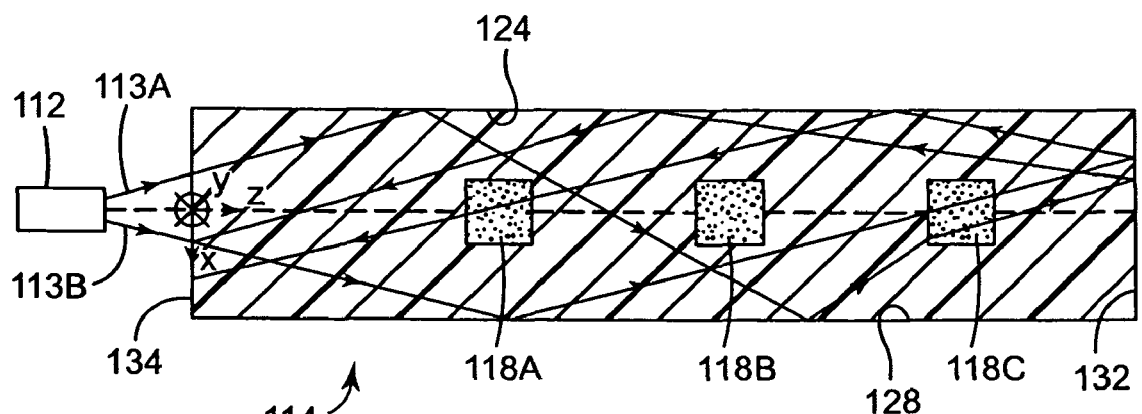
FIG. 3 is a cross sectional view of an analytical cell of the invention with microgrooves, showing the optical path of selected incoming light rays.

Referring to FIG. 3, representative light rays 113A and 113B are emitted by the decollimated source 112 and enter the cell 114 through the fourth face of the cell 134. For example, the ray 113B is initially reflected at the first internal surface 128, illuminates the third conduit 118C in the array, and is reflected back into the cell at the reflective third internal surface 132. Following reflection at the third internal surface 132, the ray 113B is again reflected at the second internal surface 124, illuminates the first conduit 118A in the array, and exits the cell 114 at the fourth face 134. The internal reflection of the surrounding cell 114 allows very efficient use of the light energy entering the cell to more uniformly illuminate all conduits in the array.

Figure 4:
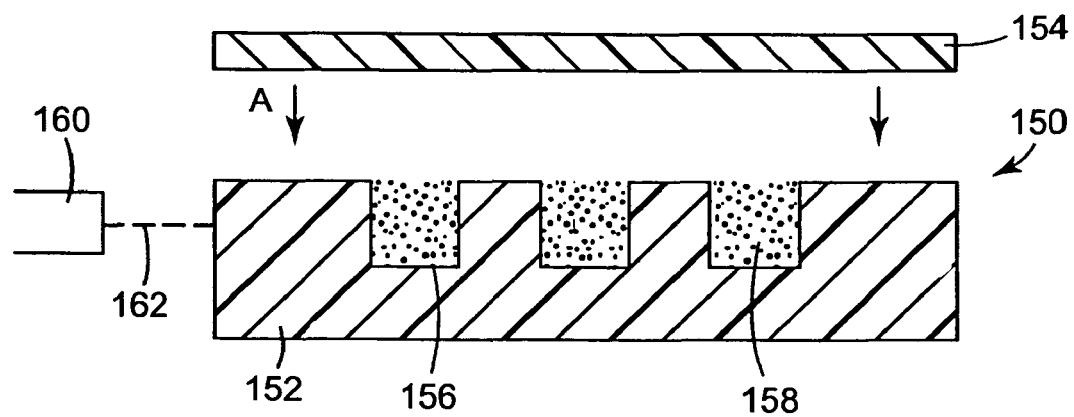
FIG. 4 is a cross sectional view of a two part analytical cell of the invention with microgrooves.

Referring to FIG. 4, an alternate embodiment of the invention is shown with a two-part fluorescence cell 150. The cell 150 includes a microstructured substrate 152 and a substantially flat cover 154. The cover 154 may be made of the same material as the substrate 152, or may be made of a different material. The substrate 152 has machined or embossed therein an array of microgrooves 156. The longitudinal axes of the microgrooves 156 are substantially parallel, and the microgrooves are substantially uniform and coplanar in the array. The microgrooves 156 are filled with a migration medium 158. When the cover is moved in the direction of arrow A and placed on the substrate 152, the cell 150 becomes a lightguide. Light 162 from a source 160 that enters the substrate 152 is internally reflected at the interior surfaces of the substrate 152 and the cover 154 to substantially uniformly illuminate the microgrooves 156 in the array. In an alternate embodiment not shown in FIG. 4, both the substrate and the cover may be microstructured to form a wide variety of cross sectional shapes for the microgrooves 156.

Figure 5:
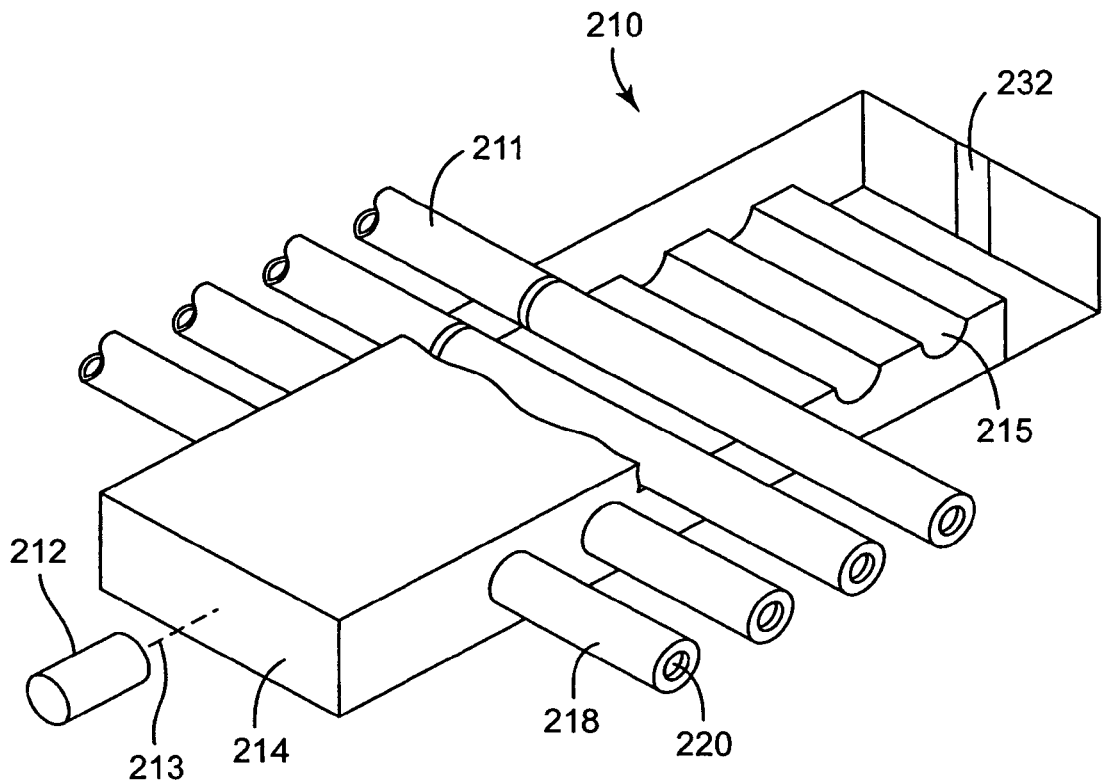
FIG. 5 is a cutaway, perspective view of an analytical cell of the invention with capillaries.

As noted above, many current electrophoresis devices use capillary arrays for high throughput analysis procedures. Referring to FIG. 5, an array of capillaries may be inserted into a lightguide structure to create an analytical cell that substantially enhances the uniformity of illumination of the individual capillaries in the array. In an electrophoresis analysis system 210 shown in FIG. 5, a coating 211 is removed from a series of capillaries 218 filled with a migration medium 220. The stripped, bare ends of the capillaries 218 are inserted into appropriately formed passages 215 in a block-like lightguide cell 214 to form a substantially coplanar array. The longitudinal axes of the capillaries 218 are substantially parallel. A light beam 213 emitted from a source 212 enters the cell 214 to uniformly illuminate the capillaries 218 and stimulating fluorescence from the fluorescently labeled analytes passing through the cell. This fluorescence is detected by a detector (not shown) to obtain analytical data regarding the analytes in the capillaries 218.

Figure 6:
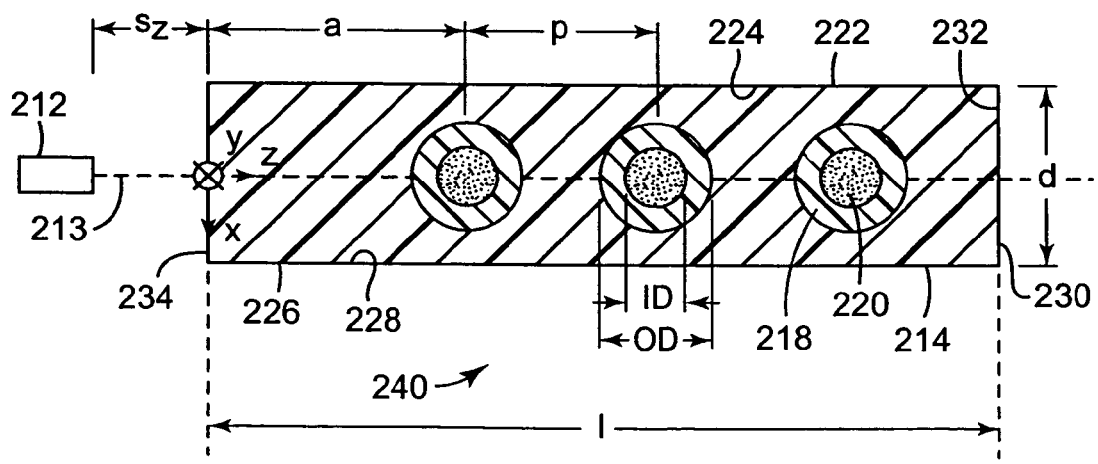
FIG. 6 is a cross sectional view of an analytical cell of the invention with capillaries.

Referring to FIG. 6, a cross-sectional view of an embodiment of a fluorescence cell 214 is shown. The cell 214 has a block-like shape with a substantially rectangular cross section having a length, l, measured in FIG. 6 along the z direction, which is substantially greater than its depth, d, measured along the x direction. The cell 214 includes three capillaries 218 having a substantially circular cross sectional shape with a selected inside diameter (ID) and outside diameter (OD). The longitudinal axes of the capillaries 218 are substantially parallel to one another at a substantially equal pitch, p, and the capillaries are arranged in a substantially coplanar array. Each capillary 218 is filled with a migration medium 220, which is typically a polymeric gel.

The cell 214 includes a first wall 222 with a first internal surface 224, as well as a substantially parallel and opposed second wall 226 with a second internal surface 228 facing the first internal surface 224. The cell 214 further includes a third wall 230 that is generally normal to the planes of the first and second walls 222, 226. The third wall 230 has an internal surface 232. Any of the internal surfaces 224, 228 and 232 may be mirrored or at least partially reflective to reflect light back into the cell 214. Preferably, at least part of the surface 232 is a mirror (See also FIG. 5).

A light source 212, typically a laser, emits a light beam 213 having an optical axis along the z direction and generally in the plane of the capillaries 218. The light source 212 is a distance $s_z$ from the cell 214, and the light beam 213 enters the cell 214 at a fourth face 234 and travels along the z direction a defined distance, the atrium, a, until it reaches the first capillary in the array.

Light rays entering the cell 214 are internally reflected and remain confined to the cell to allow substantially uniform illumination of all the capillaries in the array. Substantial internal reflection in the cell 214 results from selection of materials with appropriate refractive indices at the beam wavelength for the cell 214, the capillaries, the migration medium 220, and the surrounding medium 240. Preferably, to achieve the most uniform illumination of all the capillaries in the array, the refractive indices of the cell 214, the capillaries 218, and the migration medium 220 should match, or at least be as similar as possible, to reduce the diffusive effect of the surfaces encountered by the incoming light rays. The cell 214 is typically a block of glass or plastic, although one skilled in the art could select a wide variety of materials, depending on the wavelength emitted by the source 212, the refractive indices of the capillaries 218, the migration medium 220, the surrounding medium 240, and the fluorescence properties of the cell material. Suitable materials include fused silica glass and borosilicate glass.

Figure 7:
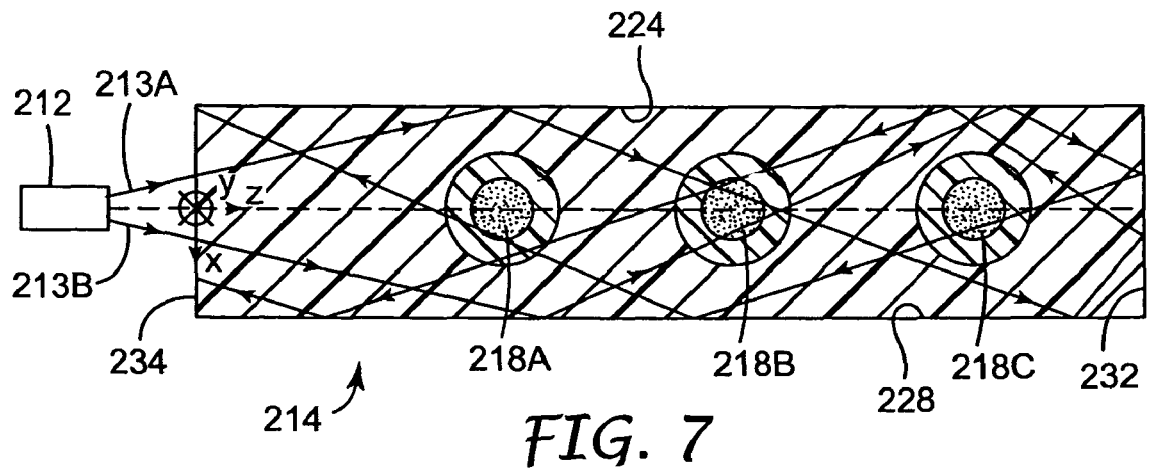
FIG. 7 is a cross sectional view of an analytical cell of the invention with capillaries, showing the optical path of selected incoming light rays.

Referring to FIG. 7, a representative light rays 213A and 213B are emitted by the decollimated source 212 and enter the cell 214 through the fourth face of the cell 234. The ray 213A is initially reflected at the first internal surface 224, illuminates the second capillary 218B in the array, and is reflected back into the cell at the reflective second internal surface 228 and the reflective third internal surface 232. Following reflection at the third internal surface 232, the ray 213A is again reflected at the first internal surface 124, illuminates the second capillary 218B in the array, is reflected at the second internal surface 228, and exits the cell through the wall 234.

The internal reflection of the surrounding cell 214 allows very efficient use of the light energy entering the cell to more uniformly illuminate all capillaries in the array. In contrast to conventional devices, the flexibility provided by internal reflection also allows a wide range of capillary inside and outside diameters. As a general rule, the design considerations discussed above with respect to cells with conduits also apply to cells using capillaries to retain the migration medium. However, the walls of the capillaries typically serve as an integral part of the lightguiding portion of the cell, particularly if their refractive indices are well matched with the refractive indices of the cell and the migration medium.

Figure 8:
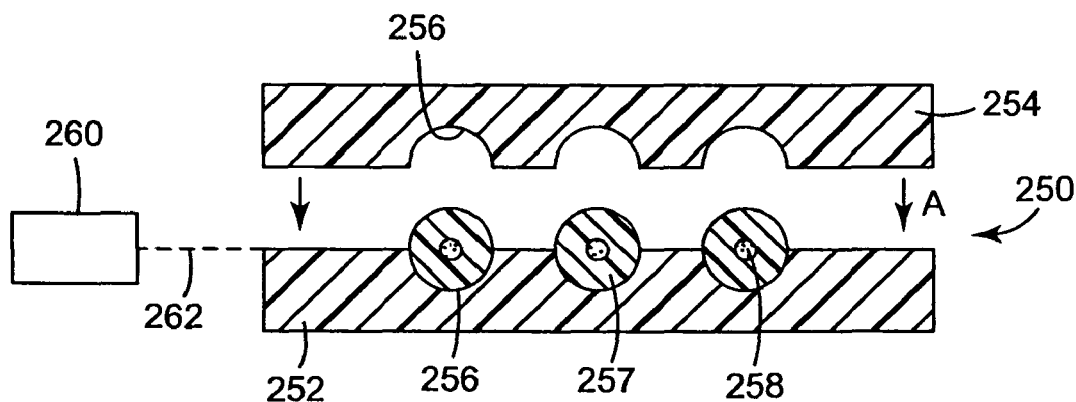
FIG. 8 is a cross sectional view of a two part analytical cell of the invention with capillaries.

Referring to FIG. 8, an alternate embodiment of the invention is shown with a two-part analytical cell 250. The cell 250 includes a microstructured substrate 252 and a corresponding microstructured cover 254. The substrate 252 and the cover 254 have formed therein an array of microgrooves 256. The longitudinal axes of the microgrooves 256 are substantially parallel, have arcuate cross sections, and are substantially uniform and coplanar in the array. In the microgrooves 256 are placed capillaries 257, each filled with a migration medium 258. When the cover is moved in the direction of arrow A and placed on the substrate 252, the cell 250 becomes a lightguide. Light 262 from a source 260 that enters the substrate 252 is substantially internally reflected at the interior surfaces of the substrate 252 and the cover 254 to substantially uniformly illuminate the capillaries 257 in the array.

Figure 9:
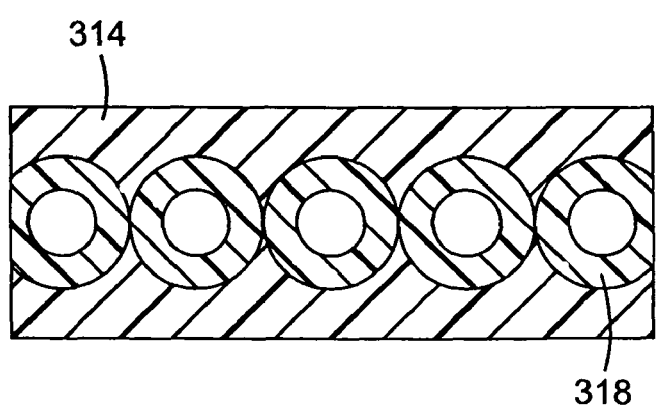
FIG. 9 is a cross sectional view of an analytical cell of the invention with close-packed capillaries.
Figure 10:
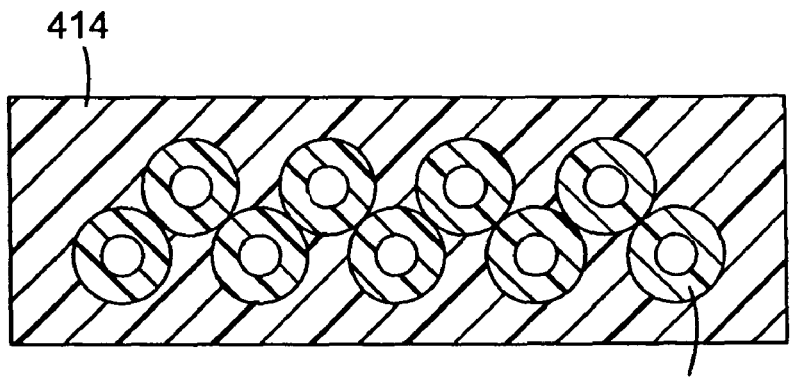
FIG. 10 is a cross sectional view of an analytical cell of the invention with close-packed, staggered capillaries.

The lightguiding properties of the cells described above allow for considerable variation in array design. The internal reflection of the cell provides sufficient illumination of the capillaries or microgrooves (also referred to generally herein as conduits) in the array, even if individual conduits are displaced by small amounts from their nominal positions. The conduits need not be placed at an even pitch, even in their nominal positions. The lightguiding properties of the cell make the arrays of the invention robust against inaccuracies in conduit placement during cell manufacture. However, referring to FIG. 9, a cell 314 with a close packed coplanar arrangement of conduits 318, with all conduits touching each other in the plane of the array, appears to provide the highest and most uniform illumination. In fact, the lightguiding properties of the cells described above provide uniform conduit illumination even for non-planar, close-packed arrangements. For example, the cell 414 illustrated in FIG. 10 includes capillaries 418 in a staggered, close-packed arrangement. This allows more conduits to be placed into a given fixed field of view of a detector such as a CCD camera, which maximizes the number of samples that can be analyzed simultaneously with one instrument.

Figure 11:
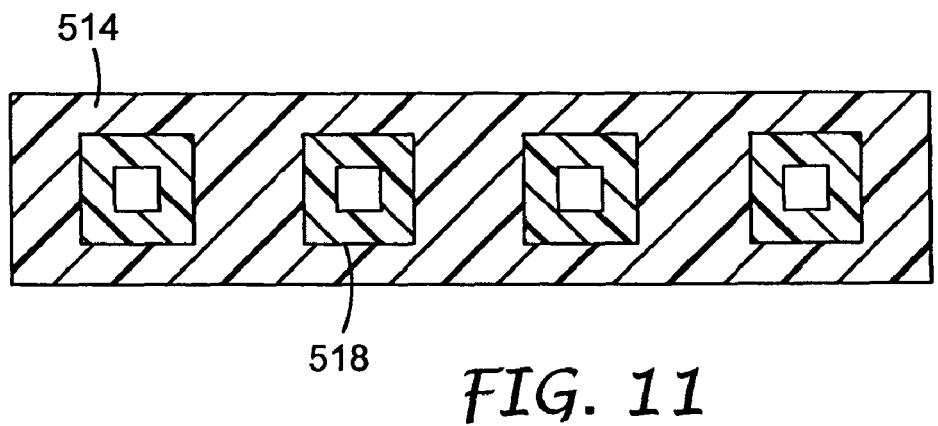
FIG. 11 is a cross sectional view of an analytical cell of the invention with capillaries having a non-circular cross sectional shape.
Figure 12:
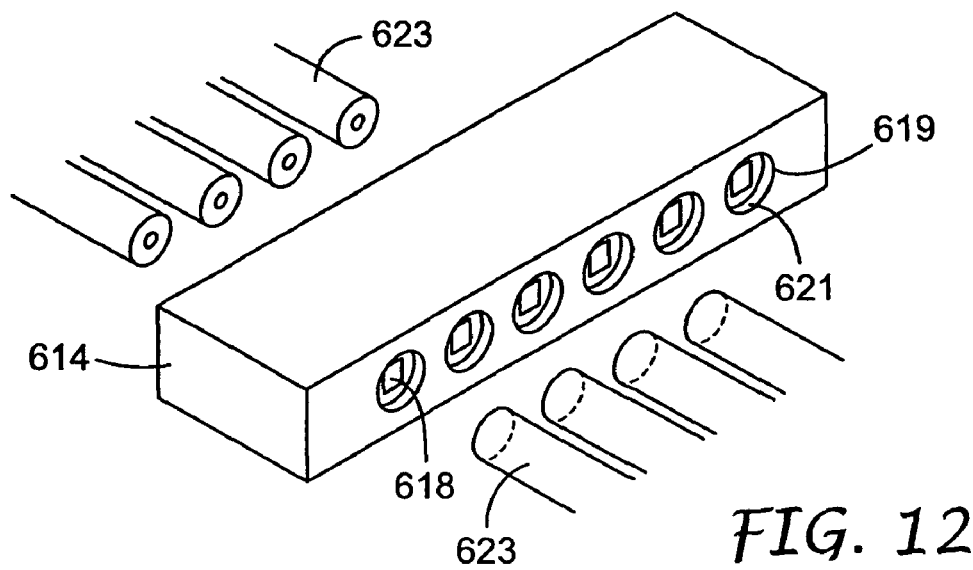
FIG. 12 is a perspective view of a analytical cell of the invention having microgrooves with a square cross sectional shape and adapted to receive capillaries having a circular cross sectional shape.

The lightguiding properties of the cells described above also accommodate a wide variety of conduit cross sectional shapes. Many different conduit cross sectional shapes are possible, such as circles, squares, rectangles, triangles, ellipses, and the like. However, conduits with square cross sections, including microgrooves and capillaries, are preferred. The square cross sectional shape appears to provide the most uniform illumination of the array, at least when the incoming light is directed in the plane of the array and normal to the longitudinal axes of the conduits. While not wishing to be bound by any theory, the square conduit is believed to present a flat face to the incoming light beam, which minimizes reflection and refraction out the cell. For example, referring to FIG. 11, a cell 514 is shown having an array of capillaries 518 with square cross sectional shapes. To take advantage of this optimized conduit shape for commonly used capillaries with a circular cross section, FIG. 12 shows a cell 614 constructed as a monolithic block with square internal microgrooves 618. The cell 614 includes recesses 619 with a circular cross section and a mating shoulder 621 to allow secure attachment of capillaries 623 to the cell 614. This design exploits the advantages of microgrooves arrays in the detection region of the cell 614, which has fewer surfaces and a square cross sectional shape to minimize refraction, but preserves the glass capillary format for analytical separations.

Figure 13A:
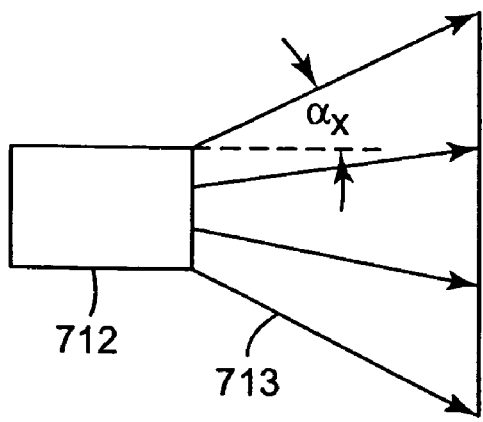
FIG. 13A and FIG. 13B are schematic representations of the incoming light beam in an analytical device of the invention.

To provide the most uniform illumination of the conduits in the cell array, it is preferred that the light beam entering the array be shaped and decollimated. As shown in FIG. 13A, a source 712 emits a beam 713 spread in the direction in the plane of the array and generally normal to the longitudinal axes of the conduits (See, for example, the x axis of FIGS. 2-3.), by an amount referred to herein as an angular value $\alpha_x$. An optimal range of the value $\alpha_x$, defined as the standard deviation of a Gaussian distribution of the launch angle, provides a homogenized light front that propagates down the cell. If $\alpha_x$ is too small, refraction at the first conduit encountered by the beam effectively "shadows" a number of the adjacent conduits in the array, which significantly decreases the illumination of the "downstream" conduits. Above an optimal value of $\alpha_x$, refraction out of the cell becomes dominant, and the overall intensity received by each conduit appears to decrease monotonically as $\alpha_x$ increases. For example, for a cell in air with a depth of 200 μm and circular capillaries with a diameter of 120 μm and placed at a pitch of 240 μm, an optimal value of $\alpha_x$ appears to be a divergence half angle of about 5° to about 50°, preferably about 10° to about 20°. The value of $\alpha_x$ may also be expressed in terms of a numerical aperture (NA) according to the equation $NA = n \sin(\alpha_x)$, where n is the refractive index of the surrounding medium. The preferred range of NA for the cell with a depth of 200 μm and circular capillaries with a diameter of 120 μm and placed at a pitch of 240 μm is about 0.09 to about 0.77, preferably about 0.17 to about 0.34.

Figure 13B:
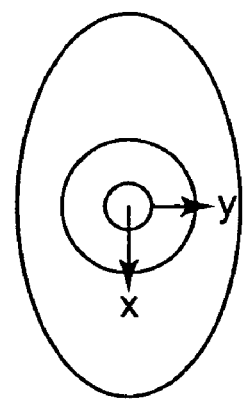

In addition, referring to FIG. 13B, beam divergence in the y direction, in the plane of the array (See, for example, the y axis of FIGS. 2-3.), referred to herein as an angular value $\alpha_y$, is preferably made small to minimize simultaneous excitation of multiple analytes, particularly in the conduits farthest away from the source. An optimal value of $\alpha_y$ appears to be a divergence half angle of approximately 1° or less.

Figure 14:
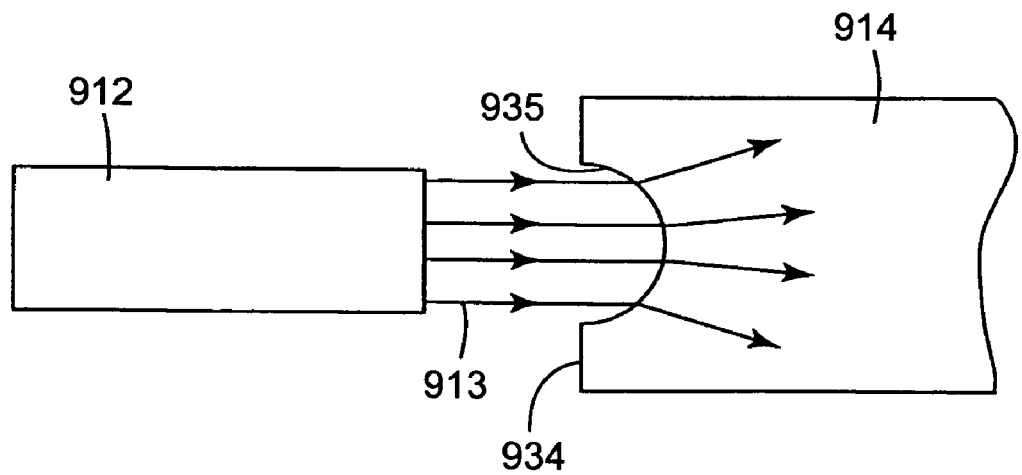
FIG. 14 is a cross sectional view of an analytical cell of the invention with a lens-like face.
Figure 15:
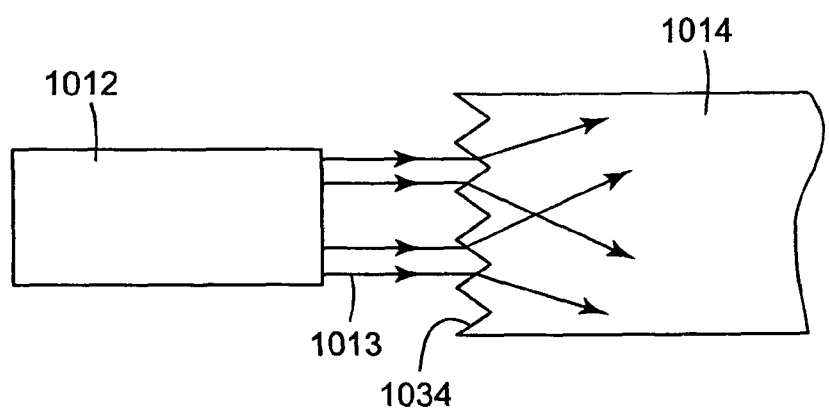
FIG. 15 is a cross sectional view of an analytical cell of the invention with a grating-like face.

The decollimation of the beam may be accomplished in many different ways. For example, an optical train may be placed between the source and the cell to provide the proper beam shape and divergence. In an alternative shown in FIG. 14, the face 934 of the cell 914 may be shaped to be a plano-concave lens 935 with an appropriate radius of curvature to provide proper beam divergence. In another alternative that would be expected to be more tolerant of misalignment between the light source and the cell, a cell 1014 is shown in FIG. 15 that includes a grating-like face 1034 that diverges the light rays 1013 entering the cell. Or, in the alternative, a diffuser may be placed in the beam path to generate divergence in the light rays entering the cell. Many other diverging cell face designs would be apparent to those of ordinary skill in the art.

Figure 16:
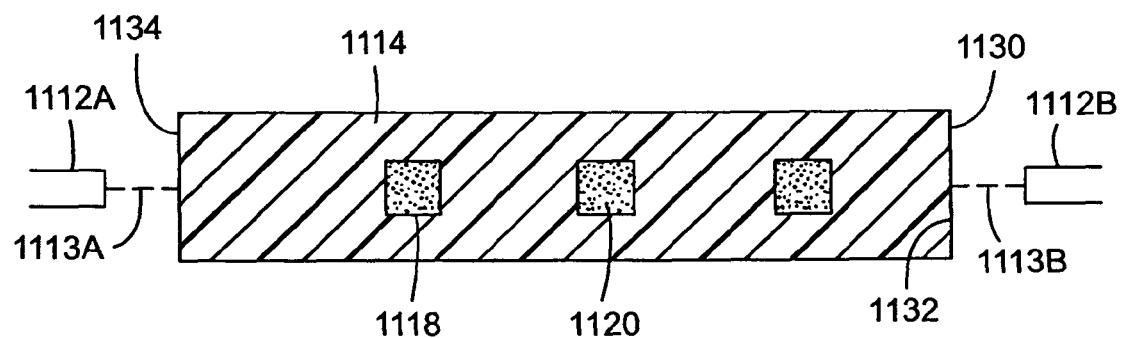
FIG. 16 is a cross sectional view of an analytical cell of the invention using two sources of illumination.

In another embodiment shown in FIG. 16, the cell 1114 may be illuminated with a first light source 1112A and a second light source 1112B placed on the opposite side of the cell. The second light source 1112B emits a light beam 1113B that enters the cell 1114 through the third face 1130 and has an optical axis that is substantially collinear with the optical axis of the beam 1113A. In this embodiment the interior surface 1132 of the third face 1130 is not reflective.

EXAMPLES

Example 1

A cell was modeled with a microgrooves configuration similar to that shown in FIGS. 2-4, using a polymer gel as the migration medium. The cell had the dimensions and material properties shown in Table 1 below.

TABLE 1

| | |
|---|---|
| Number of Microgrooves | 104 |
| Microgrooves Width w (μm) | 50 |
| Microgrooves Height h (μm) | 50 |
| Pitch (μm) | 240 |
| Cell Depth (μm) | 200 |
| Atrium (mm) | 2 |
| Beam Radius (μm) | 25 |
| Beam Divergence $\alpha_x$ (deg, x direction) | 20 |
| Beam Divergence $\alpha_y$ (deg, y direction) | 1 |
| Source Distance (sz) (μm) | 20 |
| Index of Refraction of Cell | 1.49 |
| Index of Refraction of Migration Medium | 1.41 |
| Index of Refraction of Surrounding Medium | 1 |
| Intrinsic Absorption Coefficient of Cell (1/mm) | 0.004 |
| Intrinsic Absorption Coefficient of Migration Medium (1/mm) | 0.004 |
| Intrinsic Absorption Coefficient of Surrounding Medium (1/mm) | 0 |

Figure 17:
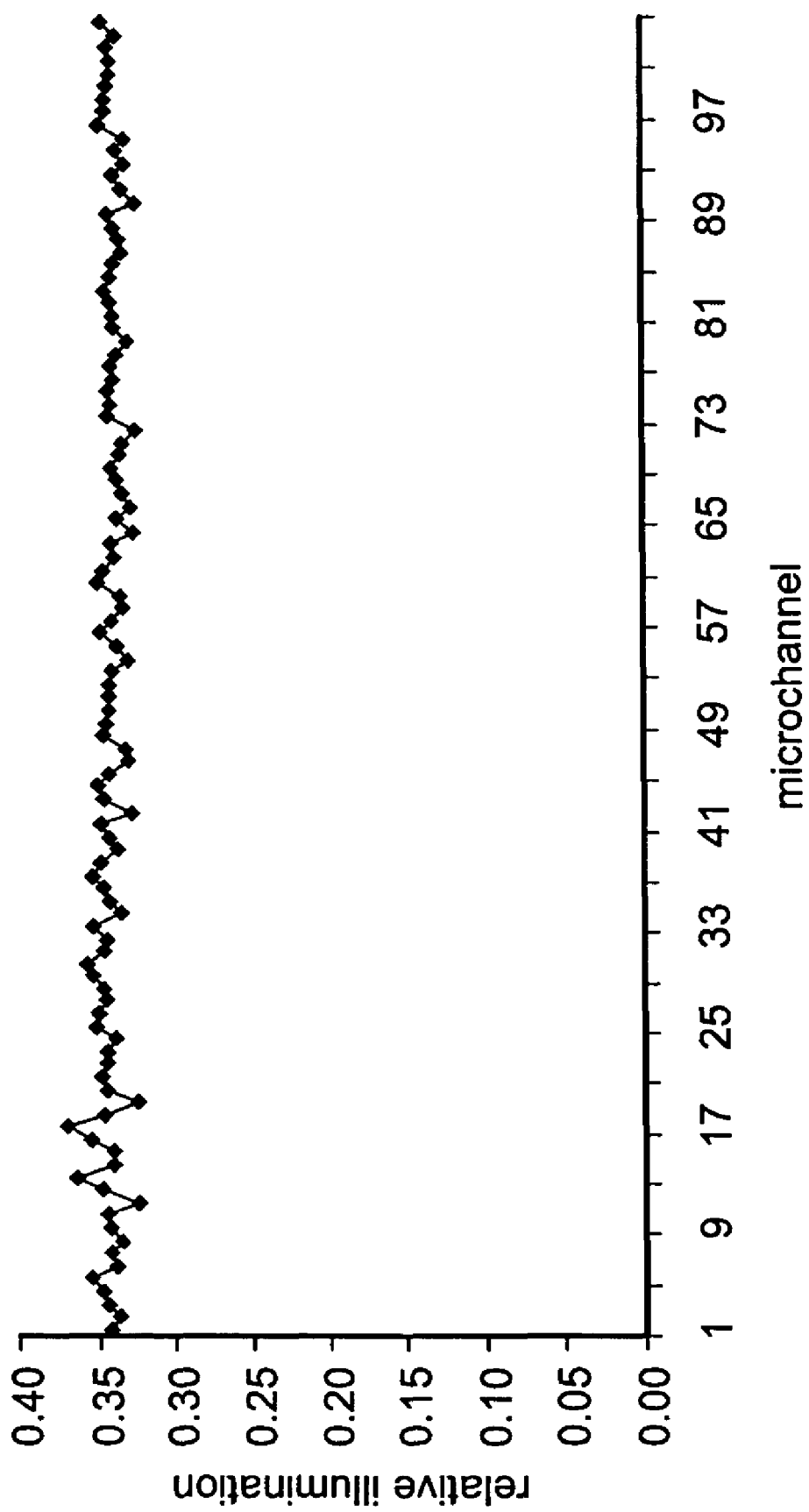
FIG. 17 is a plot of relative illumination versus microgrooves number for the array of Example 1.

This cell design was optically modeled using ray tracing simulations well known in the art. The results, which are shown in FIG. 17, are expressed in units of relative illumination, defined as the fraction of the power each microgrooves would have absorbed had a 50 μm laser beam directly illuminated the microgrooves without reflection or refraction. The microgrooves were numbered sequentially from 1 to 104, with microgrooves 1 located nearest the light source. The results indicate extremely uniform illumination for all the microgrooves in the 104 member array.

Example 2

A cell was modeled with capillaries in the general configuration shown in FIGS. 5-8, using a polymer gel as the migration medium. The cell had the dimensions and material properties shown in Table 2 below.

TABLE 2

| | |
|---|---|
| Number of Capillaries | 104 |
| Capillaries ID (μm) | 50 |
| Capillaries OD (μm) | 120 |
| Pitch (μm) | 240 |
| Cell Depth (μm) | 200 |
| Atrium (mm) | 2 |
| Beam Radius (μm) | 25 |
| Beam Divergence $\alpha_x$ (deg, x direction) | 20 |
| Beam Divergence $\alpha_y$ (deg, y direction) | 1 |
| Source Distance sz (μm) | 20 |
| Index of Refraction of Cell | 1.49 |
| Index of Refraction of Medium | 1.41 |
| Index of Refraction of Capillaries | 1.46 |
| Index of Refraction of Surrounding Medium | 1 |
| Intrinsic Absorption Coefficient of Cell (1/mm) | 0.004 |
| Intrinsic Absorption Coefficient of Migration Medium (1/mm) | 0.004 |
| Intrinsic Absorption Coefficient of Capillaries (1/mm) | 0.004 |
| Intrinsic Absorption Coefficient of Surrounding Medium (1/mm) | 0 |

Figure 18:
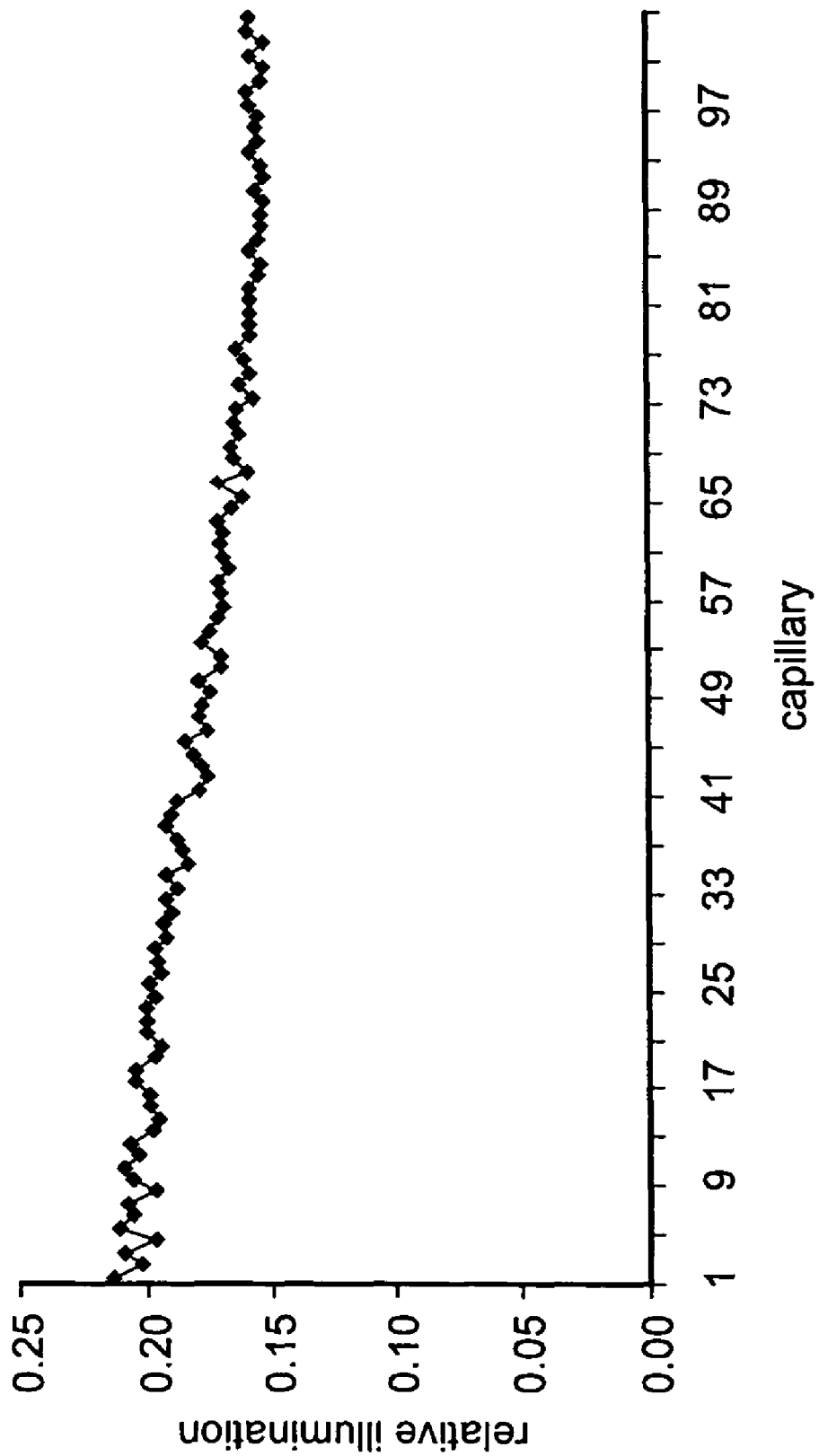
FIG. 18 is a plot of relative illumination versus capillary number for the array of Example 2.

This cell design was optically modeled using well known ray trace simulations and the criteria of Example 1. The results are shown in FIG. 18. Very uniform illumination is achieved despite the plethora of surfaces in the system. Furthermore, this comes at a reasonable cost in intensity. Overall, the 104 capillaries in the array absorb only about 0.34% of the total beam power.

Example 3

Figure 19:
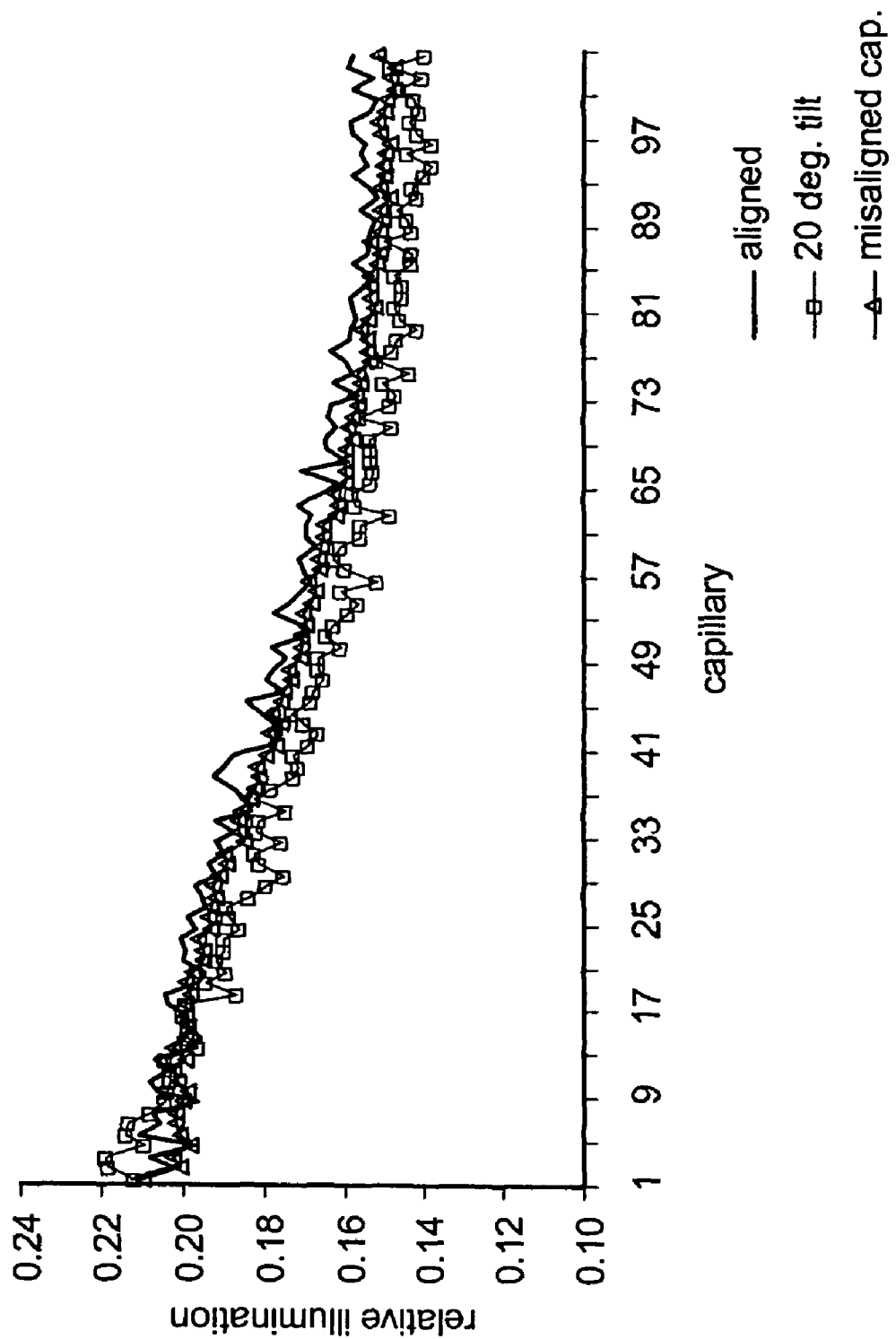
FIG. 19 is a plot of relative illumination versus capillary number for the array of Example 2 with non-optimal optical alignment of the light source and capillaries.

In this example the sensitivity of the cell performance was evaluated with regard to two common types of optical misalignment that may occur during manufacture or operation of an analytical device. First, a cell similar to that of Example 2 was modeled. A baseline relative illumination value was established using a laser light source that was properly aligned with the cell. Relative illumination was also computed for a case where the light source was tilted about 20° away from the plane of the array. In addition, relative illumination was measured for a case where all 104 capillaries were randomly displaced from their nominal locations by ±25 μm in either the x or z directions (See axes in FIG. 6). The results are shown in FIG. 19. Despite rather extreme excursions from optimum optical alignment, neither intensity nor uniformity appear to be significantly reduced.

Example 4

Figure 13B:
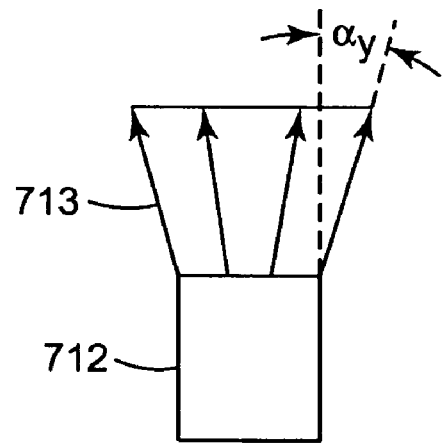
Figure 20:
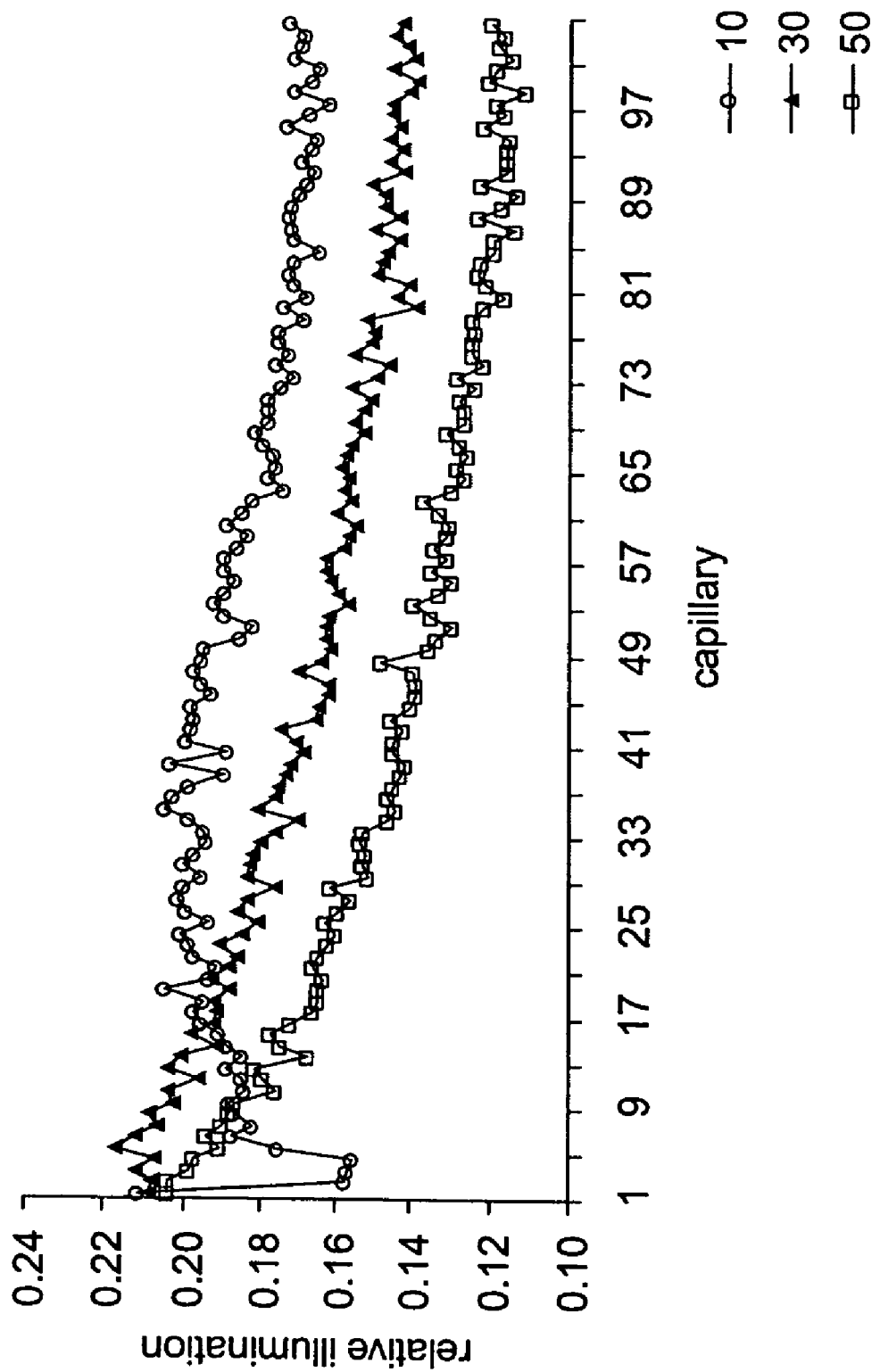
FIG. 20 is a plot of relative illumination versus capillary number for the array of Example 2 with variation in the angular spread of the incoming beam.

In this example the relative illumination intensity was evaluated with respect to variations in the angular spread of the light beam in the x direction (See axes in FIGS. 6 and 13), $\alpha_x$. Using the capillary array of Example 2, $\alpha_x$ was varied from 10° to 50°. The results are shown in FIG. 20. The results plotted in FIG. 20 indicate that if $\alpha_x$ is too small, refraction at the first conduit encountered by the beam effectively "shadows" a number of the adjacent conduits in the array, which significantly decreases illumination. Above an optimal value of $\alpha_x$, the overall intensity received by each conduit appears to decrease monotonically as $\alpha_x$ increases.

Example 5

Figure 21:
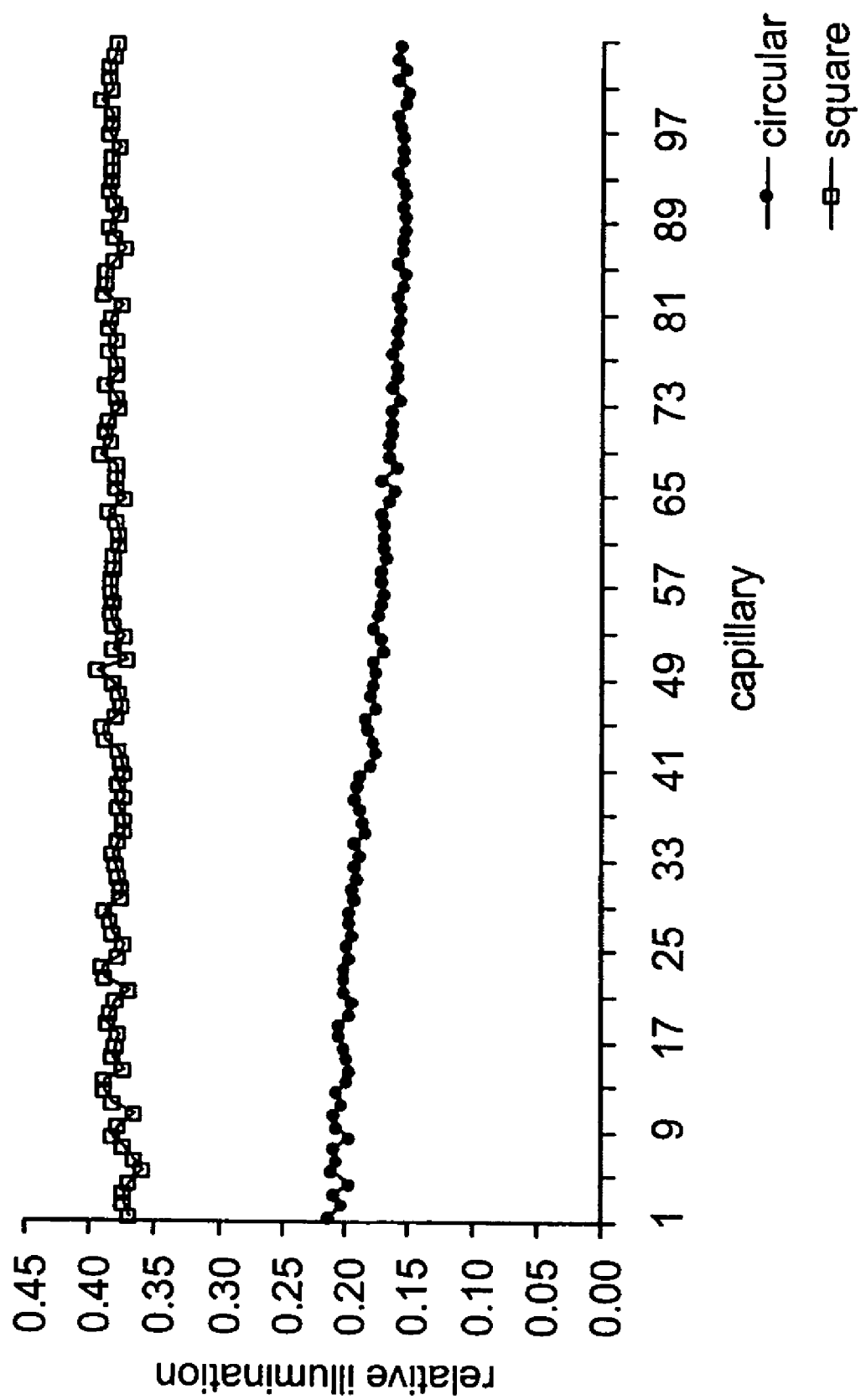
FIG. 21 is a plot comparing relative illumination versus capillary number for the array of Example 2 with that of a similar array having capillaries with a square cross sectional shape.

In this example the relative illumination values of capillaries with circular cross sections are compared to those with square cross sections. First, the array of Example 2, which had 104 capillaries with circular cross sections, was evaluated. Then a second cell was modeled with 104 capillaries having square cross sections (See FIG. 11). Both cells were evaluated using ray trace simulations well known in the art, and the results are shown in FIG. 21. As noted above, the flat faces of the square capillaries reduce out-of-plane refraction of incoming light, which enhances illumination.

Example 6

Figure 22:
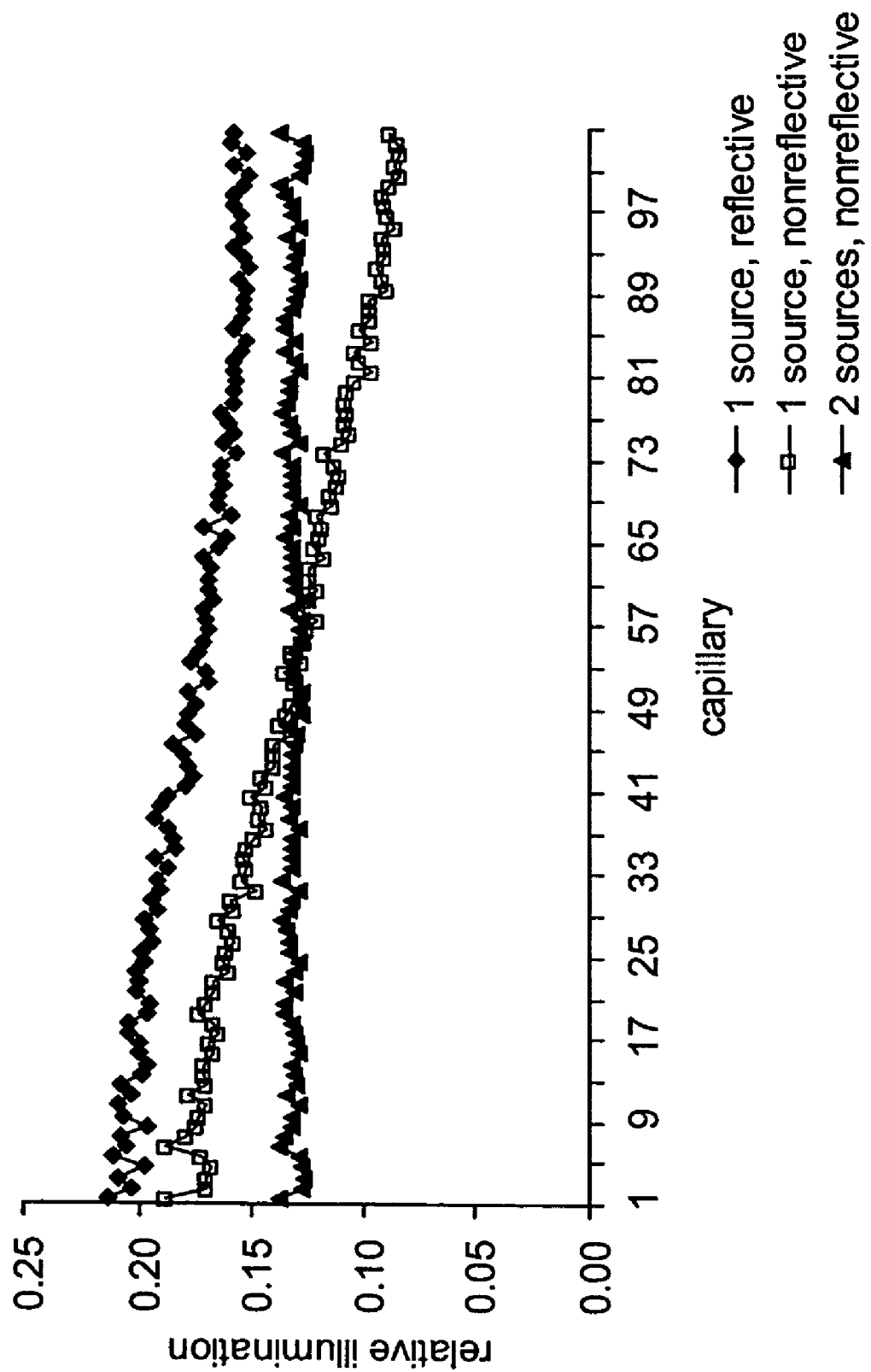
FIG. 22 is a plot of relative illumination versus capillary number for the array of Example 2 with a reflective third interior surface, compared to an otherwise identical array with a non-reflective interior surface, as well as an identical array using dual source illumination.

First, the relative illumination of the 104 capillary array of Example 2 was evaluated using ray trace simulations well known in the art. This array, as shown in FIGS. 5-8, included a reflective third interior surface 232. A second array identical to that of Example 2 except for a non-reflective third interior surface, was evaluated. A third array, similar to that shown FIG. 16, was modeled using two sources and a non-reflective interior surface 1132, and then evaluated using ray trace simulations well known in the art. The results are shown in FIG. 22. The single source device with a reflective third interior surface provided the best levels of relative illumination, followed by the dual source device. The single source device without the reflective third interior surface provided relatively poor illumination to the downstream capillaries in the array.

A number of embodiments of the invention have been described. Nevertheless, it will be understood that various modifications may be made without departing from the spirit and scope of the invention. Accordingly, other embodiments are within the scope of the following claims.

What is claimed is:
1. An analytical device, comprising:
a lightguide consisting of a solid block of a transparent or a translucent material, wherein the lightguide comprises an array of close-packed conduits extending therethrough such that all the conduits touch each other in a plane of the array, and a migration medium in the conduits;
a first light source outside the lightguide, wherein the first light source emits a first light beam in a first direction with an optical axis substantially coplanar with and normal to the longitudinal axes of the conduits,
a second light source outside the lightguide, wherein the second light source emits a second light beam in a second direction substantially collinear with and opposite to the first direction;
wherein the migration medium, the lightguide and a medium surrounding the lightguide have refractive indices selected such that light emitted by the first and second light sources is totally internally reflected within the lightguide to illuminate the migration medium in the conduits.

2. The device of claim 1, wherein the longitudinal axes of the conduits in the array are substantially parallel and coplanar.

3. The device of claim 2, wherein the longitudinal axes of the conduits in the array are at a substantially equal pitch to one another.

4. The device of claim 1, wherein the conduits have a substantially circular cross section.

5. The device of claim 1, wherein the conduits have a substantially square cross section.

6. The device of claim 1, wherein the conduits are capillary tubes.

7. The device of claim 1, further comprising a detector optically coupled with the lightguide.

8. The device of claim 1, wherein at least one of the first and second light beams are decollimated.

9. The device of claim 1, wherein the beams from the first and second light sources diverge in a direction normal to a plane containing the conduits.

10. The device of claim 9, wherein at least one of the first and second light beams has a divergence half angle of at least about 20° in a direction normal to a plane containing the conduits.

11. The device of claim 9, wherein at least one of the first and second light beams has a spread of no more than about 1° in a plane parallel to a plane containing the conduits.

12. The device of claim 1, wherein the lightguide is made of a glass selected from the group consisting of fused silica and borosilicate.

13. The device of claim 1, wherein the lightguide is a polymeric material selected from the group consisting of polycarbonate, polymethylmethacrylate, polymethylpentene, and cycloolefins.

* * * * *

UNITED STATES PATENT AND TRADEMARK OFFICE
CERTIFICATE OF CORRECTION

PATENT NO. : 8,268,249 B2  Page 1 of 1
APPLICATION NO. : 11/601326
DATED : September 18, 2012
INVENTOR(S) : Larry J. Carson et al.

It is certified that error appears in the above-identified patent and that said Letters Patent is hereby corrected as shown below:

On the Title Page, Column 2, Item [56], line 23, "Waveguids" should be
-- Waveguides --

In the Specifications

Column 2, line 52, "therethough." should be -- therethrough. --

Column 8, line 19, "$\theta 1$ and $\theta 2$," should be -- $\beta 1$ and $\beta 2$, --

Column 11, line 39, "2–3.)," should be -- 2-3), --

Column 11, line 63, "2–3.)," should be -- 2-3), --

Signed and Sealed this
Second Day of July, 2013

Teresa Stanek Rea
*Acting Director of the United States Patent and Trademark Office*